US008241672B2

(12) United States Patent
Driscoll

(10) Patent No.: US 8,241,672 B2
(45) Date of Patent: Aug. 14, 2012

(54) OMEGA-3 ENRICHED FISH OIL-IN-WATER PARENTERAL NUTRITION EMULSIONS

(75) Inventor: David F. Driscoll, Bridgewater, MA (US)

(73) Assignee: Stable Solutions LLC, Goleta, CA (US)

( * ) Notice: Subject to any disclaimer, the term of this patent is extended or adjusted under 35 U.S.C. 154(b) by 508 days.

(21) Appl. No.: 12/382,196

(22) Filed: Mar. 11, 2009

(65) Prior Publication Data
US 2010/0233280 A1   Sep. 16, 2010

(51) Int. Cl.
*A61K 35/60* (2006.01)
*A23D 9/013* (2006.01)
*A23D 7/00* (2006.01)

(52) U.S. Cl. ......... 424/523; 426/531; 426/601; 426/602
(58) Field of Classification Search .......................... None
See application file for complete search history.

(56) References Cited

U.S. PATENT DOCUMENTS

| | | | | |
|---|---|---|---|---|
| 5,698,594 A | * | 12/1997 | Breivik et al. | 514/560 |
| 5,780,451 A | * | 7/1998 | DeMichele et al. | 514/54 |
| 5,874,470 A | | 2/1999 | Nehne et al. | |
| 6,008,248 A | * | 12/1999 | Pscherer et al. | 514/560 |
| 6,020,020 A | | 2/2000 | Cain et al. | |
| 6,159,523 A | | 12/2000 | Cain et al. | |
| 7,323,206 B1 | * | 1/2008 | Driscoll et al. | 426/602 |
| 7,560,486 B2 | | 7/2009 | Carpentier et al. | |
| 2004/0247693 A1 | | 12/2004 | Carpentier et al. | |
| 2006/0127491 A1 | * | 6/2006 | Puder et al. | 424/523 |

FOREIGN PATENT DOCUMENTS

| | | |
|---|---|---|
| DE | 196 48 566 A1 | 6/1997 |
| EP | 1 279 400 A1 | 1/2003 |
| EP | 1 408 931 B1 | 3/2009 |
| WO | WO 90/08544 A1 | 8/1990 |
| WO | WO 97/19683 A1 | 6/1997 |
| WO | WO 03/009828 A1 | 2/2003 |

OTHER PUBLICATIONS

Yvon Carpentier et al., "Rapid Cellular Enrichment of Eicosapentaenoate After a Single Intravenous Injection of a Novel Medium-Chain Triacylglycerol:Fish-Oil Emulsion in Humans," American Journal of Clinical Nutrition, Feb. 10, 2010, pp. 1-8, doi: 10.3945/ajcn.2009.27951, American Society for Nutrition, Bethesda, Maryland, USA.
Notification of Transmittal of the International Search Report and the Written Opinion of the International Searching Authority, or the Declaration (Form PCT/ISA/220), International Search Report (Form PCT/ISA/210), and Written Opinion of the International Searching Authority (Form PCT/ISA/237), dated Jan. 6, 2011, issued in corresponding International Application No. PCT/US2010/000723.
Abulrob et al., *The effect of fatty acids and analogues upon intracellular levels of doxorubicin in cells displaying P-glycoprotein mediated multidrug resistance*, 8(4) J Drug Target 247-256 (2000) (abstract only).

Calviello et al., *Docosahexaenoic acid enhances the susceptibility of human colorectal cancer cells to 5-fluorouracil*, 55(1) Cancer Chemother Pharmacol 12-20 (Jan. 2005) (abstract only).
Elzinga et al., *Modification of experimental nephrotoxicity with fish oil as the vehicle for cyclosporine*, 43(2) Transplantation 271-274 (Feb. 1987) (abstract only).
Fracasso et al., *Phase 1 and pharmacokinetic study of weekly docosahexaenoic acid-paclitaxel, Taxoprexin, in resistant solid tumor malignancies*, 63(3) Cancer Chemother Pharmacol 451-458 (Feb. 2009) (abstract only).
Futamura, *Toxicity of amiodarone on mouse pulmonary endothelial cells cultured with or without alveolar macrophages*, 21(4) J Toxicol Sci 253-267 (Nov. 1996) (abstract only).
Germain et al., *Anthracycline-induced cardiac toxicity is not increased by dietary omega-3 fatty acids*, 47(2) Pharmacol Res 111-117 (Feb. 2003) (abstract only).
Heller et al., *Omega-3 fatty acids improve the diagnosis-related clinical outcome*, 34(4) Crit Care Med 972-979 (Apr. 2006) (abstract only).
Julien et al., *Postmortem brain fatty acid profile of levodopa-treated Parkinson disease patients and parkinsonian monkeys*, 48(5) Neurochem Int, 404-414 (Apr. 2006) (abstract only).
Mahéo et al., *Differential sensitization of cancer cells to doxorubicin by DHA: a role for lipoperoxidation*, 39(6) Free Radic Biol Med 742-751 (Sep. 2005) (abstract only).
Menendez et al., *Exogenous supplementation with omega-3 polyunsaturated fatty acid docosahexaenoic acid (DHA; 22:6n-3) synergistically enhances taxane cytotoxicity and down regulates Her-2/neu (c-erbB-2) oncogene expression in human breast cancer cells*, 14(3) Eur J Cancer Prev 263-270 (Jun. 2005) (abstract only).
Priyamvada et al., *Studies on the protective effect of dietary fish oil on gentamicin-induced nephrotoxicity and oxidative damage in rat kidney*, 78(6) Prostaglandins Leukot Essent Fatty Acids 369-381 (Jun. 2008) (abstract only).
Rudra et al., *Cell-specific enhancement of doxorubicin toxicity in human tumour cells by docosahexaenoic acid*, 21(1A) Anticancer Res 29-38 (Jan.-Feb. 2001) (abstract only).
Wang et al., *Synthesis and preliminary antitumor activity evaluation of a DHA and doxorubicin conjugate*, 16(11) Bioorg Med Chem Lett 2974-2977 (Jun. 1, 2006) (abstract only).
Wichmann et al., *Evaluation of clinical safety and beneficial effects of a fish oil containing lipid emulsion (Lipoplus, MLF541): data from a prospective, randomized, multicenter trial*, 35(3) Crit Care Med 700-706 (Mar. 2007) (abstract only).
Yang et al., *Attenuation of ciclosporin-induced nephrotoxicity by dietary supplementation of seal oil in Sprague-Dawley rats*, 57(11) J Pharm Pharmacol 1485-1492 (Nov. 2005) (abstract only).
Bougnoux et al., *Improving outcome of chemotherapy of metastatic breast cancer by docosahexaenoic acid: a phase II trial*, 101(12) Br J Cancer 1978-1985 (Dec. 15, 2009).
Colas et al., *Sensitization by dietary docosahexaenoic acid of rat mammary carcinoma to anthracycline: a role for tumor vascularization*, 12(19) Clin Cancer Res 5879-5886 (Oct. 1, 2006).

(Continued)

Primary Examiner — Chris R Tate
Assistant Examiner — Douglas F White
(74) Attorney, Agent, or Firm — Buchanan Ingersoll & Rooney PC

(57) ABSTRACT

A composition is provided which includes an enriched fish oil as a lipid source. Also provided is a composition which includes a fatty acid of a fish oil and a medium-chain triglyceride, wherein the composition is an oil-in-water emulsion.

20 Claims, No Drawings

OTHER PUBLICATIONS

Ding et al., *Differential sensitivity of cancer cells to docosahexaenoic acid-induced cytotoxicity: the potential importance of down-regulation of superoxide dismutase 1 expression*, 3(9) Mol Cancer Ther 1109-1117 (Sep. 2004).

Gonzalez-Periz et al., *Docosahexaenoic acid (DHA) blunts liver injury by conversion to protective lipid mediators: protectin D1 and 17S-hydroxy-DHA*, 20(14) FASEB J 2537-2539, E1844-E1855 (Dec. 2006).

Harries et al., *Phase I/II study of DHA-paclitaxel in combination with carboplatin in patients with advanced malignant solid tumours*, 91(9) Br J Cancer 1651-1655 (Nov. 1, 2004).

Manni et al., *The impact of fish oil on the chemopreventive efficacy of tamoxifen against development of N-methyl-N-nitrosourea-induced rat mammary carcinogenesis*, 3(3) Cancer Prev Res (Phila PA) 322-330 (Mar. 2010).

Matta et al., *TRPV1 is a novel target for omega-3 polyunsaturated fatty acids*, 578(Pt 2) J Physiol 397-411 (Jan. 15, 2007).

"PrestoBlue™ Cell Viability Reagent", Life Technologies, http://www.invitrogen.com/site/us/en/home/brands/Molecular-Probes/Key-Molecular-Probes-Products/PrestoBlue-Cell-Viability-Reagent.html, 2012, Life Technologies Corporation.

Mansour, N. R., et al., "Comparison of microscopy and alamar blue reduction in a larval based assay for schistosome drug screening," *PloS Negl Trop Dis*, Aug. 2010, 4(8):e795, PubMed (Abstract only).

Nociari, M.M., et al., "A novel one-step, highly sensitive fluorometric assay to evaluate cell-mediated cytotoxicity," *J Immunol Methods*, Apr. 1998, 213(2):157-67, PubMed (Abstract only).

Hamid, R., et al., "Comparison of alamar blue and MTT assays for high through-put screening," *Toxicol in Vitro*, Oct. 2004, 18(5):703-10, PubMed (Abstract only).

Van Der Harst, M.R., et al., "Gentamicin Nephrotoxicity—A Comparison of In Vitro Findings with In Vivo Experiments in Equines," *Veterinary Research Communications*, 2005, 29(3), pp. 247-261, Springer.

Al-Nasiry, S., et al., "The use of Alamar Blue assay for quantitative analysis of viability, migration and invasion of choriocarcinoma cells," *Human Reproduction*, May 2007, 22(5):1304-09, Epub Feb. 16, 2007, PubMed (Abstract only).

Sykes, M.L., et al., "Development of an Alamar Blue™ Viability Assay in 384-Well Format for High Throughput Whole Cell Screening of *Trypanosoma brucei brucei* Bloodstream Form Strain 427," *Am J Trop Med Hyg*, 2009, 81(4), pp. 665-674, The American Society of Tropical Medicine and Hygiene.

Calder, P.C., et al., "The 2008 ESPEN David Cuthbertson Lecture: Fatty acids and inflammation—from the membrane to the nucleus and from the laboratory bench to the clinic," *Clin Nutr*, Feb. 2010, 29(1):5-12, PubMed (Abstract only).

Extended Search Report issued by the European Patent Office issued in corresponding European Patent Application No. 10751124.8 dated Feb. 1, 2012.

Bougnoux et al., *"Improving Outcome of Chemotherapy of Metastatic Breast Cancer by Docosahexaenoic Acid: a Phase II Trial,"* British Journal of Cancer, 2009, vol. 101, No. 12, pp. 1978-1985, Cancer Research UK.

Driscoll, *"Lipid Injectable Emulsions: Pharmacopeial and Safety Issues,"* Pharmaceutical Research, Sep. 2006, vol. 23, No. 9, pp. 1959-1969, Springer Science + Business Media, Inc.

Driscoll, Letter to the Editor, Journal of Parenteral and Enteral Nutrition, Jul./Aug. 2009, vol. 33, No. 4, pp. 451-452, Sage, The American Society for Parenteral & Enteral Nutrition.

Lowell et al., *"Postoperative Fluid Overload: Not a Benign Problem,"* Crit Care Med, Jul. 1990;18(7):728-733, PubMed (Abstract only).

Mathru et al., *"Effect of Fast vs Slow Intralipid Infusion on Gas Exchange, Pulmonary Hemodynamics, and Prostaglandin Metabolism,"* Clinical Investigations in Critical Care, Chest, Feb. 1991, 99, pp. 426-429, American College of Chest Physicians.

Prasertsom, et al., *"Pulmonary Vascular Resistance During Lipid Infusion in Neonates,"* Arch Dis Child, 1996;74:F95-98, Children's Health Centre and Perinatal Research Centre, University of Alberta.

Ling et al., *"Inflammatory Mediators in Patients Receiving Long-Term Home Parenteral Nutrition,"* Digestive Disease Science, Nov. 2001;46(11):2484-9, PubMed (Abstract only).

Driscoll et al., *"The Influence of Medium-chain Triglycerides on the Stability of All-In-One Formulations,"* International Journal of Pharmaceutics, 240 (2002), pp. 1-10, Elsevier Science B.V.

Bistrian, *"Clinical Aspects of Essential Fatty Acid Metabolism; Jonathan Rhoads Lecture,"* Journal of Parenteral and Enteral Nutrition, 2003, vol. 27, No. 3, pp. 168-175, Sage, The American Society for Parenteral & Enteral Nutrition.

Gura et al., *"Use of a Fish Oil-Based Lipid Emulsion to Treat Essential Fatty Acid Deficiency in a Soy Allergic Patient Receiving Parenteral Nutrition,"* Clinical Nutrition, Oct. 2005;24(5):839-47, PubMed (Abstract only).

Wales et al., *"Neonatal Short Bowel Syndrome: A Cohort Study,"* Journal of Pediatric Surgery, May 2005;40(5):755-62, PubMed (Abstract only).

Paquot et al., *"Fatty Liver in the Intensive Care Unit,"* Curr Opin Clin Nutr Metab Care, Mar. 2005;8(2):183-87, PubMed (Abstract only).

Lee et al., *"Saturated, but Not n-6 Polyunsaturated, Fatty Acids Induce Insulin Resistance: Role of Intramuscular Accumulation of Lipid Metabolites,"* J Appl Physiol, May 2006;100(5):1467-74, PubMed (Abstract only).

Gura et al., *"Reversal of Parenteral Nutrition-Associated Liver Disease in Two Infants With Short Bowel Syndrome Using Parenteral Fish Oil: Implications for Future Management,"* Pediatrics, Jul. 2006, vol. 118, No. 1, pp. e197-e201, American Academy of Pediatrics.

Stanley et al., *"UK Food Standards Agency Workshop Report: The Effects of the Dietary N-6: n-3 fatty Acid Ratio on Cardiovascular Health,"* British Journal of Nutrition, Dec. 2007; 98(6):1305-1310, PubMed (Abstract only).

Wanten et al., *"Immune Modulation by Parenteral lipid Emulsions[1,2],"* American Journal of Clinical Nutrition 2007;85:1171-84, American Society for Nutrition.

Driscoll et al., *"Pharmacopeial Compliance of Fish Oil-Containing Parenteral Lipid Emulsion Mixtures: Globule Size Distribution (GSD) and Fatty Acid Analyses,"* International Journal of Pharmaceutics, 379 (2009), pp. 125-130, Elsevier B.V.

Wang et al., *"ω-3 Fatty Acids—Supplemented Parenteral Nutrition Decreases Hyperinflammatory Response and Attenuates Systemic Disease Sequelae in Severe Acute Pancreatitis: A Randomized and Controlled Study,"* Journal of Parenteral and Enteral Nutrition, May/Jun. 2008, vol. 32, No. 3, pp. 236-241, Sage, The American Society for Parenteral & Enteral Nutrition.

Simoens et al., *"Inclusion of 10% Fish Oil in Mixed Medium-Chain Triacylglycerol-Long-Chain Triacylglycerol Emulsions Increases Plasma Triacylglycerol Clearance and Induces Rapid Eicosapentaenoic Acid (20:5n—3) Incorporation Into Blood Cell Phospholipids[1,3],"* American Journal of Clinical Nutrition 2008;88:282-88, American Society for Nutrition.

*"Globule Size Distribution in Lipid Injectable Emulsions,"* United States Pharmacopoeia 32, Chapter <729>, 2009, Physical Tests, pp. 283-285.

*"Fish Oil, Rich in Omega-3 Acids, Piscis oleum Omega-3 Acidis abundans,"* European Pharmacopoeia 6.0, 01/2008:1912, 2008, Monograph 1912, pp. 1893-1895.

*"Omega-3-Acid Triglycerides: Omega-3 Acidorum Triglycerida,"* European Pharmacopoeia 5.4, 01/2005:1352 corrected, 2005, Monograph 1352, pp. 3995-3997.

*"Triglycerides, Medium-Chain, Triglycerida Saturata Media,"* European Pharmacopoeia 6.0, 01/2008:0868, 2007, Monograph 0868, pp. 3122-3124.

Friesecke et al., *"Fish oil supplementation in the parenteral nutrition of critically ill medical patients: a randomised controlled trial,"* Intensive Care Med, Aug. 2008;34(8):1411-20, Epub Mar. 21, 2008, PubMed (Abstract only).

Calder, *"Rationale and use of n-3 fatty acids in artificial nutrition"* Proc Nutr Soc, Nov. 2010;69(4):565-73, Epub May 5, 2010, Erratum in Proc Nutr Soc, May 2011;70(2):282, PubMed (Abstract only).

Driscoll, Copending U.S. Appl. No. 13/255,828, filed Nov. 1, 2011, entitled, "Omega-3 Enriched Fish Oil-in-Water parenteral Nutrition Emulsions".

Driscoll, Copending U.S. Appl. No. 12/923,257, filed Sep. 10, 2010, entitled, "Method of Mitigating Adverse Drug Events Using Omega-3 Fatty Acids as a Parenteral Therapeutic Drug Vehicle".

Driscoll, Copending U.S. Appl. No. 13/230,316, filed Sep. 12, 2011, entitled, "Method of Mitigating Adverse Drug Events Using Omega-3 Fatty Acids as a Parenteral Therapeutic Drug Vehicle".

* cited by examiner

OMEGA-3 ENRICHED FISH OIL-IN-WATER PARENTERAL NUTRITION EMULSIONS

BACKGROUND

1. Field

The present disclosure relates to oil-in-water (o/w) parenteral lipid emulsions that have a novel composition containing, for example, mainly two oils.

2. Related Art

Oil-in-water parenteral emulsions have been used clinically for nutritional and medical purposes. Of the various types of oils used, historically soybean oil was first introduced almost 50 years ago and thus has the greatest clinical experience.

SUMMARY

According to an exemplary aspect, a composition is provided including an enriched fish oil as a lipid source.

According to another exemplary aspect, a composition is provided including an omega-3 essential fatty acid (EFA) and an omega-6 essential fatty acid of a fish oil, wherein the essential fatty acids are present in an amount effective to minimize an impact of excessive pro-inflammatory fatty acids.

According to another exemplary aspect, a composition is provided including a medium-chain fatty acid (FA) of a medium-chain triglyceride (MCT) oil, wherein the medium-chain fatty acid is present in amount effective to facilitate a metabolic clearance of fish oil.

According to another exemplary aspect, a composition is provided including medium-chain triglycerides of an oil, wherein the medium-chain triglycerides are present in an amount effective to facilitate stability.

According to another exemplary aspect, a composition is provided including a fatty acid of a fish oil and a medium-chain triglyceride, wherein the composition is an oil-in-water emulsion comprising an oil phase and an aqueous phase.

DETAILED DESCRIPTION

An exemplary embodiments is directed to a novel parenteral lipid emulsion composition comprising: high concentrations of fish oil highly enriched in n3-FAs; minimal, but sufficient amounts of n6-FAs to meet EFA requirements; and low concentrations of saturated MCTs in a final mixture that is stable, has normal metabolic clearance, and is well-tolerated by patients.

An exemplary first oil is derived from fish, rich in the polyunsaturated and bioactive omega-3, or n-3 fatty acids (n3-FA). For example, the fish oil can be present from about 31% to about 90%, or from about 40% to about 80%, or from about 50% to about 70%, or from about 60% to about 65%, based on the total weight of the oil component of the emulsion. They can be 20- to 22-carbon compounds and can contain 3 or more double bonds located at the $3^{rd}$ position from the methyl end of the long-chain fatty acid (LCFA) molecule. Standard notation for the various fatty acids (FAs) includes: 1) carbon number, followed by, 2) the number of double bonds, and ending with 3) the position of the double bond relative to the methyl position (or "n3" in the case of the LCFA from fish oil). In particular, the marine oil can be highly enriched with two major n3-FAs, i.e., eicosapentaenoic acid, or EPA (20:5n3), and docosahexaenoic acid, or DHA (22:5n3). The marine oil can contain lesser amounts of other n3-FAs, such as docosapentaenoic acid, or DPA (22:6n3).

The fish oil component of the o/w parenteral lipid emulsion can represent oils from a mixture of fatty fish families, such as from the following species: Engraulidae (e.g., anchovies), Carangidae (e.g., mackerel), Clupeidae (e.g., herring), Osmeridae (e.g., smelt), Salmonidae (e.g., salmon) and Scombridge (e.g., tuna). In the European Pharmacopeia (EP), there are two monographs (i.e., EP 1352 entitled "Omega-3 Acid Triglycerides", and, EP 1912 entitled "Fish Oil, Rich in Omega-3 Acids") that pertain to fish oil (EP 1352, EP 1912, 2008). The monograph EP 1352 substantially differs from EP 1912 in that the composition and requirements for the bioactive n3-FAs are much higher (EP 1352: EPA+DHA 45%; total n3-FAs 60% vs. EP 1912: EPA: 13%; DHA 9%; total n3-FAs 28%). The levels of n3-FAs in EP 1912 are consistent with those found in nature, whereas in EP 1352, the n3-FA concentrations are not natural and therefore require an enrichment process such as molecular distillation, whereby certain undesirable LCFAs that are present, for example, myristic and palmitoleic acids, are removed. In so doing, the concentrations of all FAs present, and particularly the n3-FAs, are proportionately elevated (Driscoll, 2008a). Fish oil also can contain an adequate amount of n6-FA, arachidonic acid or AA (20:4n6), and/or a modest amount of linoleic acid or LA (18:2n6) and/or alpha linolenic acid or ALA (18:3n3).

An exemplary second component of the oil phase in the proposed o/w parenteral lipid emulsion can include the group of saturated medium chain triglycerides (MCTs). For example, the MCT oil can be present from about 10% to about 69%, or from about 20% to about 60%, or from about 30% to about 50%, or from about 40% to about 45%, based on the total weight of the oil component of the emulsion. For example, this oil, which can be derived from plants, can primarily contain caprylic acid (50 to 80%), an 8-carbon saturated FA (8:0), and capric acid (20 to 50%), a 10-carbon saturated FA (10:0). The description of the MCT for use in this disclosure can meet the requirements of EP monograph 0868, entitled "Triglycerides, Medium Chain" (Triglycerida saturate media) (EP 0868, 2008). Additional components included in the o/w parenteral emulsions described may include small amounts of soybean oil, rich in the n6-FA, LA and lesser amounts of the n3-FA, ALA. Other pharmaceutical ingredients can also be included such as, for example, egg phospholipids, sodium oleate, glycerol, alpha tocopherol, sodium hydroxide and/or sterile water for injection. Such ingredients can be used to stabilize the emulsion and make suitable its use for intravenous administration in accordance with pharmacopeial specifications. Inclusion of these ingredients has been approved as such for use in o/w parenteral emulsions that have been approved for human use.

Oil-in-water parenteral emulsions can be used clinically for nutritional and medical purposes. Of the various types of oils used, historically soybean oil was first introduced almost 50 years ago and thus has the greatest clinical experience, but more recent formulations can include other oils, such as MCT, fish and olive oils. As a nutritional supplement, o/w parenteral emulsions are intended for use in patients having a dysfunctional gastrointestinal tract, originating from, for example, mesentery artery thrombosis, requiring a massive small bowel resection that produces a condition known as "short bowel syndrome". Consequently, such patients have insufficient intestine and therefore are incapable of absorbing sufficient macronutrients (protein, carbohydrate and fat) and micronutrients (electrolytes, vitamins and minerals). There are other clinical indications for intravenous nutrition (e.g., radiation enteritis, bowel obstruction, high output ileostomies, etc.) that will also require life-long intravenous nutrition. In other clinical cases, intravenous nutrition is used as a temporary therapeutic maneuver, for example, as in critically ill patients to support the body's metabolic response to injury and infection. In the absence of oral intake, these catabolic conditions can produce large daily losses of vital body protein and profound energy deficits. If prolonged or accompanied by pre-existing malnutrition, the absence of nutritional intervention may increase the risk of significant clinical morbidity or mortality (Driscoll, 2008b).

In the case of o/w parenteral emulsions containing fish oil, these emulsions can provide the essential fatty acids (EFAs) from both the n-3 FA, EPA, DHA and the n-6 FA, AA, which cannot be synthesized by the body. In the case of parenteral o/w emulsions containing soybean oil, these emulsions can provide the precursors to these EFAs in the form of ALA for n3-FAs and LA for n6-FAs. Again, the introduction of soybean oil was based on providing sufficient concentrations of ALA (7 to 11%) and very high amounts of LA (50 to 55%) to prevent EFA deficiency. To meet the EFA requirements with soybean oil-based parenteral emulsions, between 1 and 4% of daily minimum calories are required (Bistrian, 2003). Thus, for example, in a 2000 kcal adult diet, 1% of caloric intake (as LA or ~50% of soybean oil) would translate to approximately 40 kcals, or a minimum of about 3.5 g of soybean oil per day (equal to 17.5 mLs of a 20% lipid emulsion); for a 100 kcal neonate diet, 1% of caloric intake would translate to 2 kcal (about 0.2 g per day, or 1 mL of the soybean oil emulsion) in order to meet EFA requirements.

In addition to being a source of EFAs, parenteral lipid emulsions can also be prescribed as a daily source of energy or calories, often in substitution of a portion of the calories that would be provided as carbohydrate (hydrated dextrose or glucose), administered intravenously. The practice of prescribing both glucose and lipids as energy sources (or a "mixed-fuel system") can be done to avoid significant metabolic complications associated with high doses of intravenous glucose. These include hyperglycemia and increased infectious risks, hepatic damage from the metabolic conversion of glucose to fat in the liver, increased respiratory dysfunction from excessive carbon dioxide production associated with hepatic lipogenesis in patients with impaired lung function, and other adverse effects. As a daily source of calories, fat intake from parenteral lipid emulsions is commonly prescribed in amounts ranging between 20 and 40% of total caloric intake. Thus, for example, in a 2000 kcal adult diet, this represents 400 to 800 kcals, or approximately 44 to 88 g per day, which is equal to about 220 to 440 mLs per day of a 20% oil-in-water emulsion. For a neonatal diet of 100 kcals per day, this would equate to 20 to 40 kcals, or approximately 2.2 to 4.4 g per day, equal to about 10 to 20 mLs per day of the same 20% lipid emulsion.

Although a soybean oil-based parenteral emulsion was the first safe intravenous o/w dispersion introduced in 1961, and therefore the formulation most widely used worldwide, soybean oil is not the optimal lipid to use in the clinical setting. As a long-chain triglyceride (LCT) of plant origin, the most abundant "omega" fatty acid found in this oil is the polyunsaturated, essential (precursor) n6-FA, LA (50-55%), followed by the monounsaturated, non-essential n9-FA, oleic acid (18:1n9) (24-26%), followed by the polyunsaturated essential (precursor) n3 FA, ALA. Due to the dominant presence of the n6-FA LA, and considering both its pro-inflammatory role and the fact that it is a precursor to the highly vasoactive "2-series" eicosanoids involving prostaglandins and thromboxanes, as well as the potent immunomodulatory "4-series" leukotrienes, soybean oil may adversely accentuate the systemic inflammatory response and/or exacerbate the deterioration of certain functions of vital organs. During critical illness accompanied by systemic inflammatory response syndrome (SIRS), for example, the "2-series" eicosanoids produced from the infusion of soybean oil-based parenteral emulsions may worsen lung function in patients with respiratory distress syndrome. In adults, for example, infusions of soybean oil-based lipid emulsions have produced two different adverse effects on the lungs, which have been shown to be infusion rate-dependent (Mathru et al, 1991). In one case, infusions of 100 g of a 20% soybean oil-based parenteral emulsion (i.e., 500 mL) over 10 hours was associated with significantly increased shunt fraction from pre-infusion levels presumably via prostaglandin-mediated pulmonary vasodilatation. This action is counter to the normal physiologic response when blood flow proportionately decreases to poorly ventilated segments of the lung during respiratory distress, known as hypoxic pulmonary vasoconstriction. This results in an unphysiologic mismatch between the normal balance between ventilation and perfusion in the lungs, where the body now makes futile attempts to perfuse poorly ventilated areas of the lung. In contrast, the same infusion, but now infused over only 5 hours, produced the opposite effect, i.e., vasoconstriction, evidenced by significant increases in mean pulmonary artery pressure, which could also aggravate respiratory function by augmenting the hypoxic pulmonary vasoconstrictive response to potentially pathological proportions (e.g., pulmonary hypertension). Similar adverse pulmonary responses have been associated with the infusion of parenteral lipid emulsions rich in n6-FAs in infants (Prasertsom et al, 1996).

Another clinical example demonstrating the potential deleterious effects associated with the administration of conventional soybean oil-based parenteral emulsions, rich in the pro-inflammatory n6-FAs, involves hepatoxicity. For example, in acutely ill infants with SIRS, prolonged infusion of soybean oil-based parenteral emulsions may induce a pathological condition known as parenteral nutrition-associated liver disease or PNALD. The PNALD condition often occurs with long-term use of parenteral nutrition in infants and may lead to liver failure and the need for liver transplantation. Clinical findings associated with PNALD include abnormal elevations of blood components observed in liver function tests, such as serum transaminases, bilirubin and alkaline phosphatase, due to hepatic fat accumulation, leading ultimately to organ failure (Gura et al, 2006). The mechanism of liver injury is not completely understood but has been suggested to occur by a "two-hit" theory. The first "hit" occurs during the accumulation of fat in the liver, or hepatic steatosis. The second "hit" that follows occurs in a series of subsequent steps beginning with inflammation and cellular degeneration, followed by production of reactive oxygen species or peroxidation products causing oxidative stress, that ultimately causes damage of liver tissue (Paquot et al, 2005). In infants developing PNALD, mortality approaches 100% within one year of the diagnosis (Wales et al., 2005). Adverse effects to the liver from chronic exposure to soybean oil parenteral emulsions have been linked to adults requiring long-term parenteral nutrition (Ling et al, 2001).

Clearly, therefore, parenteral lipid emulsions containing high amounts of triglycerides rich in n6-FAs are not optimal, and are associated with significant adverse events in patients requiring intravenous nutrition. Therefore, development of alternative lipid sources that decrease the concentration of n-6 FAs and their accompanying pro-inflammatory effects may be of great clinical benefit. The use of n9-FAs found in olive oil, such as the monounsaturated fatty acids produce the "1-series" of prostaglandins, thromoboxanes and leukotrienes, that are less pro-inflammatory, may be of significant benefit. The use of n3-FAs, however, such as the polyunsaturated fatty acids producing the "3-series" eicosanoids, may be of the greatest clinical benefit. In fact, the latter n3-FAs from the important omega families of fatty acids that have shown great promise and are the least pro-inflammatory, have also been shown to possess favorable effects on vital organs, and produce important immunomodulatory effects (Wanten, 2007). Thus, the ideal parenteral lipid emulsion would be one that is stable, provides a sufficient supply of the EFAs, provides a dense source of energy or calories, minimizes the adverse effects from pro-inflammatory FAs, improves functions of vital organs, and possesses therapeutically beneficial immunomodulatory effects, particularly during acute illness.

Exemplary embodiments disclosed herein employ a new composition of matter containing oils, for example, from MCT and LCTs, with novel doses of the various saturated medium-chain fatty acids (for example, 8- to 10-carbon MCFA) and, mainly unsaturated long-chain fatty acids (for example, 18- to 22-carbon LCFA) from the biologically important, essential FAs from n3 and n6 families. The final oil composition of the parenteral o/w lipid emulsion, the resulting oil phase can be made as a simple "physical" mixture or blend of the desired oils. Alternatively, specifically customized mixtures of "structured" triglycerides can be made via hydrolysis of FAs from the glycerol backbones of different oils, followed by random transesterification producing both preferred as well as analog triglyceride combinations. Or, the "structured" triglycerides can be made via enzymatic synthesis by selected lipases that are region-specific, e.g., sn-1 and sn-3 positions, and FA-specific, producing a purer form of chemically defined structured triglycerides. No mater how they are prepared, the resulting emulsions are composed of mixtures of various triglycerides and fatty acids, primarily from fish oil and MCT oil, and are mixed in specific proportions. In either case, when provided within the ranges and specifications of Table 1, the formulations can yield novel final lipid mixtures that serve as: 1) a dense source of calories, containing: 2) a highly enriched fish oil as the major lipid source; 3) minimum, but sufficient, amounts of the omega-6 fatty acids; 4) sufficient amounts of MCT oil to facilitate its metabolic clearance upon intravenous infusion; 5) sufficient amounts of MCT oil to facilitate the stability of the emulsion; and/or 6) optionally, a small fraction of soybean oil as an additional source of essential fatty acids for omega-6 requirements.

The preferred final concentration of triglycerides in the formulation can be 20% oil-in-water, and assuming 1 g of water equals 1 mL, there can be 20 g of oils per 100 mL of sterile water for injection. The composition of the final formulation can be customized to optimize the ratios of all ingredients to address a wide array of clinical and pharmaceutical issues. In addition, a given formulation may also desirably contain a specific ingredient, or set of specific ingredients, for the purpose of addressing one or more particular medical conditions and/or pharmaceutical purposes, thus yielding several variations in composition to produce several different formulations. Therefore, a wide concentration range of fish oil and MCT oil, the major constituent triglycerides in exemplary formulations, is indicated in Table 1, designed potentially to provide different treatment options.

Table 2 provides a sample of various oil combinations, expressed as weight percentages of each of the triglycerides. In an exemplary embodiment, only highly-enriched fish oil, in compliance with EP monograph 1352 (EP 1352, 2008), can be the fish oil source along with a certain amount of MCT oil, also in compliance with EP monograph 0868 (EP 0868, 2008), to comprise the total lipid fraction (20 g of oil per 100 mL of sterile water for injection, SWFI) in the current application. In an exemplary embodiment, there is an option to also include up to 10%, or 2 g, of soybean oil per 20 g of total oil per 100 mL of SWFI, for example, in the event that this choice is deemed clinically advantageous or necessary to increase the dose of the omega-6 FAs in a given formulation. In exemplary embodiments, the amount of soybean oil can be restricted to comprise no more than about 10% of the total oil profile, whereas in current formulations, concentrations of soybean oil vary from 20 to 100% of the oil phase. For example, the soybean oil can be present from 0% to about 10%, or from about 1% to about 9%, or from about 2% to about 8%, or from about 3% to about 7%, or from about 4% to about 6%, based on the total weight of the oil component of the emulsion. There are numerous combinations and permutations that can be derived from the present compositions. Therefore, it should be understood that those specific combinations represented in Table 2 are merely intended to illustrate representative combinations and are not meant to be inclusive or restrictive in any way. Hence, the possibility of additional variations would be clear to those skilled in the art.

For example, the fish oil emulsion intended in this application can be one that contains a high concentration or the highest concentration of the bioactively important n3-FAs, for example, best able to deliver a wide range of potential clinical benefits by altering lipids in the blood and the structure and function of cell membranes. Providing higher amounts of n3-FAs in relation to n6-FA intakes can result in displacement of AA in cell membranes with EPA, and a shift away from the highly vasocactive and pro-inflammatory eicosanoids of the "2-series" in favor of the less vasoactive "3-series". These actions can lead to a favorable modulation of the metabolic and immune response to injury and infection, particularly in various scenarios in the acute care setting (e.g., multiple organ failure, head trauma, sepsis, burns and inflammatory bowel disease). Thus, the source (and subsequent dose) of fish oil intended in this application can have substantial effects, and the minimum concentration specified can be equal to the sum of EPA+DHA≧45% of the n3-FA profile, and the total n3-FA content (e.g., EPA+DHA+DPA)≧60%. This specification is in conformance with the requirements of EP monograph 1352 (EP 1352, 2008). Of the three current, commercially available products containing fish oil, two comply with the lower limits (i.e., EPA≧13%; DHA≧9%; Total n3-FA≧28%) associated with EP monograph 1912 (EP 1912, 2008). The concentration of fish oil in the only currently available formulation that meets EP 1352 is only 10% by weight of the oil phase, whereas in this application, for example, the minimum fraction of the oil phase containing the highly enriched fish oil can be 31%. The amount of bioactive n3-FAs in fish oil described in this disclosure can be more than double the amounts more commonly found for clinical use as specified by the two variable EP monographs (e.g., EP 1352, total n3-FA:≧60%; vs. EP 1912, total n3-FA: ≧28%).

One objective of an exemplary formulation is to deliver a high concentration or the highest concentrations of enriched fish oil available that meets a high standard or the highest pharmacopeial standards, for example, in order to maximize the clinical benefits of the n3-FAs in a variety of clinical conditions, such as the systemic inflammatory response syndrome, or SIRS, characteristically found in critically ill patients. In fact, the blood concentrations of C-reactive protein, a biomarker of SIRS, was found to be significantly reduced in critically ill patients with pancreatitis receiving n3-FAs, as compared to those patients receiving lipids as n6-FAs (Wang, 2008). As inflammation accompanies all forms of acute metabolic stress, the delivery of highly concentrated n3-FAs may reduce inflammation and improve outcome. Moreover, since fluid overload is also a major problem in the intensive care unit, use of highly concentrated n3-FAs would reduce the volume burden. In addition, the total dose of lipids required would be only one-half the amount according to this disclosure for current emulsions that conform to EP 1912, compared to using a fish oil source as detailed in this application that meets the higher specifications of EP 1352.

Exemplary formulations described in this disclosure can be designed to contain a sufficient amount of the essential FAs associated with (or obtained from): 1) n3 family, i.e., EPA (20:5n3), DHA (22:6n3) and small amounts of its precursor, linolenic acid (18:3n3); and, 2) the omega-6, or n6, family, arachidonic acid (20:4n6) or AA, as well as small amounts of its precursor, linoleic acid (18:2n6). With regard to meeting the essential n3-FA requirements, this can be easily met by both the recommended concentrations of fish oil in the formula, as well as from a highly enriched source of n3-FAs, as per the specifications of EP 1352. The amount of the essential n6-FA requirement can be specifically designed to be minimized in exemplary formulations, but in modest amounts that prevent EFA deficiency. To meet the n-6 FA requirements, these can be achieved through the use of a fish oil-MCT mixture, owing to the fact that the average amount of AA found in fish oil is approximately 0.5%. Therefore, because the amount of FA needed as M is approximately one-tenth the dose required if provided through its precursor, LA, EFA requirements are met. To prevent EFA deficiency via LA by parenteral administration, at least 1% of the total daily caloric intake should be provided (Bistrian, 2003). As stated previously, in a 2000 kcal per day diet, the minimum intake of LA would be 2.2 g per day, or approximately 3.5 g of soybean oil (~55% LA); in terms of AA, the requirements for the same diet would be approximately 0.2 g per day; in a 1500 kcal per day diet, 1.6 g of LA, or ~0.16 g of AA, per day would be needed; in a 1000 kcal per day diet, 1.1 g of LA, or ~0.11 g of AA, would be needed; in a 500 kcal per day diet, 0.55 g of LA, or ~0.05 g of AA would be needed; and finally, in a 100 kcal per day diet, 0.11 g of LA would be needed, or 0.01 g as AA per 100 calories. As can be seen in Table 3, which provides sample compositions for Fish Oil-MCT mixtures only, the EFA requirements for n6-FAs, coming from AA in the fish oil, would be met in the 80% fish oil-20% MCT oil mixture as presented. This does not include the additional source of n6-FAs that comes from the LA normally present in fish oil. It should also be recognized that certain compositions or formulations of "Lipomega-3 MCT" products may not be intended for patients susceptible to EFA deficiency, but rather for short-term parenteral administration during critical illness. In other cases, where EFA supplementation is a clinical concern, alternative formulations could be devised that contain very low amounts of soybean oil (for example, up to 10%) of the total oil phase. Table 4 provides sample formulations using a fixed 60:40 ratio (by weight) of fish oil to MCT oil, with increasing fractions of soybean oil, ranging from 1 to 5%. The "fixed" fish oil-MCT in Table 4 is merely illustrative and not meant to be exclusive or restrictive in any way as to the various oil ratios possible from this disclosure.

A preferred final concentration of oil in exemplary formulations is a 20% oil-in-water emulsion (20 g oil mixture per 100 mL). This overall oil concentration can be consistent with the oil concentration in administered lipid emulsions used clinically, and it can be associated with better plasma clearance compared to "10%" formulations, as the optimum phospholipid-triglyceride (PL:TG) ratio for parenteral lipid emulsions appears to be 0.06 (1.2 g PL: 20 g TG) (Driscoll et al., 2001). Nonetheless, there are multiple variations in the final concentration of oil in mixtures that can be devised in exemplary embodiments, as long as the PL:TG ratio of 0.06 is maintained. A sample of the possible formulations are shown in Table 5.

The concentrations of MCT oil in various possible formulations can be sufficient to facilitate the clearance of the long-chain triglycerides in fish oil (20-carbon EPA and 22-carbon DHA), which has been shown to occur in other mixtures (Simoens et al., 2008). The ratio of MCT to omega-3 LCTs in this application can be different than in other parenteral lipid emulsion mixtures containing both of these oils. For this reason, the amounts used in this application are unique and the resulting formulations can benefit from assessment to confirm the favorable effect on plasma clearance of LCTs in the presence of MCTs. Additionally or alternatively, the clearance of these formulations can be facilitated by optimizing the infusion rate to its metabolic clearance.

The concentrations of MCT oil in the various possible formulations can be sufficient to facilitate the physicochemical stability of the long-chain triglycerides in fish oil (20-carbon EPA and 22-carbon DHA), which has been shown to occur in other mixtures. (Driscoll et al., 2002). The ratio of MCT to omega-3 LCTs proposed in this application can be different than that which is found in other parenteral lipid emulsion mixtures containing both of these oils. For this reason, the relative and absolute amounts of each type of oil that are used in this application can be unique and the resulting formulations can benefit from assessment to confirm the favorable effect on emulsion stability of LCTs in the presence of MCTs.

Relatively speaking, the parenteral lipid emulsions may also contain a very small fraction of soybean oil as an additional source of n6-FAs, in addition to the amounts present in fish oil. This action may be indicated whenever EFA deficiency is considered to pose a significant clinical risk, such as in the patients receiving life-long parenteral nutrition support. In this patient population, nutrient deficiencies can develop, for example, if there is little to no gastrointestinal absorption of nutrients via oral intake. In this circumstance, a higher intake of n6-FAs via parenteral lipid emulsion may be desirable. Table 4 provides a sample of possible formulations, where the soybean oil content is increased progressively up to a level of 5% of the total lipid profile. In addition, inclusion of higher n3-FA proportions (up to 90%) in various possible formulations can also increase n6-FA intake as well.

Exemplary formulations produced as described herein can be designed to provide a unique, but dense, source of calories that are, for example, equally nitrogen-sparing as conventional or current parenteral lipid emulsions. The final parenteral lipid formulation can ideally be an isotonic energy source that can be provided in small volumes when possible. This can be particularly advantageous, for example, in the case of acutely ill patients who may be volume-overloaded as a result of receiving multiple intravenous fluids for medical purposes, such as for resuscitation and maintenance of blood pressure, kidney function and intravenous medications.

The examples described herein are not meant to be inclusive, but instead have been utilized in order to form exemplary embodiments of the disclosure. It should be understood that manipulation of specific concentrations of total ingredients, including, for example, specific compositions and proportions of each ingredient within the specified concentration ranges, may be advantageous in order to achieve a specific optimal outcome. In the present disclosure, exemplary aspects can yield unique parenteral lipid emulsions appropriate for special medical purposes.

Tables mentioned herein are set forth below:

TABLE 1

Compositions of LipOmega-3 MCT 20%

| *PHARMACEUTICAL INGREDIENT | CONCENTRATION (g/L) **(80% F.O.:20% MCT) | ***RANGE OF CONCENTRATIONS (g/L) |
|---|---|---|
| Fish Oil Major FAs | 160 | 62 to 180 |
| (36.5%) EPA (20:5n3) | 58.4 | 22.6 to 65.7 |
| (25.3%) DHA (22:6n3) | 40.5 | 15.7 to 45.5 |
| (7.0%) DPA (20:6n3) | 11.1 | 4.0 to 12.6 |
| (0.50%) AA (20:4n6) | 0.8 | 0.31 to 0.9 |
| MCT Oil | 40 | 20 to 138 |
| Soybean Oil Major FAs | 0 | 0 to 10 |
| (55%) (18:2n6) | 0 | 0.0 to 5.5 |
| (10%) (18:3n3) | 0 | 0.0 to 1.0 |
| Glycerol | 22.5 | 20 to 25 |
| Egg Phospholipids | 12 | PL:TG Ratio, 0.06 |
| Sodium Oleate | 2.5 | 0 to 3 |
| α-tocopherol | 0.2 | 0 to 1 |
| Sterile Water for Inj. | q.s. ad 1000.0 | Fixed |

*INGREDIENT Ranges:
Fish Oil: 31 to 90%;
MCT Oil: 10 to 69%;
Soybean Oil: 0 to 10%;
Glycerol: 2.0 to 2.5%;
**Sample Formulation and g per L
***GENERAL CALCULATED RANGE:
RANGES of Ingredients; not accounting for experimental errors in measurement.

TABLE 2

Sample Compositions of Possible Oil Combinations of LipOmega-3 MCT 20%

| Sample | Fish Oil (%) | MCT Oil (%) | Soybean Oil (%) |
|---|---|---|---|
| 1 | 90 | 10 | 0 |
| 2 | 80 | 20 | 0 |
| 3 | 70 | 30 | 0 |
| 4 | 60 | 40 | 0 |
| 5 | 50 | 50 | 0 |
| 6 | 40 | 60 | 0 |
| 7 | 31 | 69 | 0 |
| 8 | 90 | 9 | 1 |
| 9 | 80 | 18 | 2 |
| 10 | 70 | 27.5 | 2.5 |
| 11 | 60 | 37 | 3 |
| 12 | 50 | 46.5 | 3.5 |
| 13 | 40 | 56 | 4 |
| 14 | 31 | 64 | 5 |

TABLE 3

EFA Intakes from Sample LipOmega-3 MCT Formulations Fish Oil-MCT Oil Mixtures

| Kcals/day (20% Fat) | *Linoleic 2.2% | *Linolenic 1.5% | AA | EPA | DHA |
|---|---|---|---|---|---|
| 20 g (100 mL) of a Fish Oil 80% - MCT Oil 20% Mixture | | | | | |
| 100 (2.2 g) | 0.038 g | 0.026 g | 0.009 g | 0.64 g | 0.45 g |
| 500 (11.1 g) | 0.195 g | 0.133 g | 0.044 g | 3.24 g | 2.25 g |
| 1000 (22.2 g) | 0.391 g | 0.266 g | 0.089 g | 6.48 g | 5.62 g |
| 1500 (33.3 g) | 0.586 g | 0.399 g | 0.133 g | 9.72 g | 8.42 g |
| 2000 (44.4 g) | 0.781 g | 0.533 g | 0.178 g | 12.96 g | 11.23 g |
| 20 g (100 mL) of a Fish Oil 70% - MCT Oil 30% Mixture | | | | | |
| 100 (2.2 g) | 0.033 g | 0.023 g | 0.008 g | 0.56 g | 0.39 g |
| 500 (11.1 g) | 0.171 g | 0.117 g | 0.039 g | 2.84 g | 1.97 g |
| 1000 (22.2 g) | 0.342 g | 0.233 g | 0.078 g | 5.67 g | 3.93 g |
| 1500 (33.3 g) | 0.513 g | 0.350 g | 0.117 g | 8.51 g | 5.90 g |
| 2000 (44.4 g) | 0.684 g | 0.466 g | 0.155 g | 11.34 g | 7.86 g |
| 20 g (100 mL) of a Fish Oil 60% - MCT Oil 40% Mixture | | | | | |
| 100 (2.2 g) | 0.029 g | 0.020 g | 0.007 g | 0.48 g | 0.33 g |
| 500 (11.1 g) | 0.147 g | 0.100 g | 0.033 g | 2.43 g | 1.68 g |
| 1000 (22.2 g) | 0.293 g | 0.200 g | 0.067 g | 4.86 g | 3.37 g |
| 1500 (33.3 g) | 0.440 g | 0.300 g | 0.100 g | 7.29 g | 5.05 g |
| 2000 (44.4 g) | 0.586 g | 0.400 g | 0.133 g | 9.72 g | 6.74 g |
| 20 g (100 mL) of a Fish Oil 50% - MCT Oil 50% Mixture | | | | | |
| 100 (2.2 g) | 0.024 g | 0.017 g | 0.006 g | 0.40 g | 0.28 g |
| 500 (11.1 g) | 0.122 g | 0.083 g | 0.028 g | 2.03 g | 1.40 g |
| 1000 (22.2 g) | 0.244 g | 0.167 g | 0.056 g | 4.05 g | 2.81 g |
| 1500 (33.3 g) | 0.366 g | 0.250 g | 0.083 g | 6.08 g | 4.21 g |
| 2000 (44.4 g) | 0.488 g | 0.333 g | 0.111 g | 8.10 g | 5.62 g |
| 20 g (100 mL) of a Fish Oil 40% - MCT Oil 60% Mixture | | | | | |
| 100 (2.2 g) | 0.019 g | 0.013 g | 0.004 g | 0.32 g | 0.22 g |
| 500 (11.1 g) | 0.098 g | 0.067 g | 0.022 g | 1.62 g | 1.12 g |
| 1000 (22.2 g) | 0.195 g | 0.133 g | 0.044 g | 3.24 g | 2.25 g |
| 1500 (33.3 g) | 0.293 g | 0.200 g | 0.067 g | 4.86 g | 3.37 g |
| 2000 (44.4 g) | 0.391 g | 0.266 g | 0.089 g | 6.48 g | 4.49 g |

*Amounts of omega-6 FAs are averages from fish families in monograph 1352.

TABLE 4

EFA Intakes from Sample LipOmega-3 MCT Formulations Fish Oil-MCT Oil-Soya Oil Mixtures

| Kcals/day (20% Fat) | *Linoleic | *Linolenic | AA | EPA | DHA |
|---|---|---|---|---|---|
| 20 g (100 mL) of Fish Oil 60% - MCT Oil 39% - Soya Oil 1% | | | | | |
| 100 (2.2 g) | 0.041 g | 0.022 g | 0.007 g | 0.48 g | 0.33 g |
| 500 (11.1 g) | 0.208 g | 0.110 g | 0.033 g | 2.43 g | 1.68 g |
| 1000 (22.2 g) | 0.415 g | 0.222 g | 0.067 g | 4.86 g | 3.37 g |
| 1500 (33.3 g) | 0.623 g | 0.333 g | 0.100 g | 7.29 g | 5.05 g |
| 2000 (44.4 g) | 0.830 g | 0.444 g | 0.133 g | 9.72 g | 6.74 g |
| 20 g (100 mL) of Fish Oil 60% - MCT Oil 38% - Soya Oil 2% | | | | | |
| 100 (2.2 g) | 0.053 g | 0.024 g | 0.007 g | 0.48 g | 0.33 g |
| 500 (11.1 g) | 0.269 g | 0.122 g | 0.033 g | 2.43 g | 1.68 g |
| 1000 (22.2 g) | 0.537 g | 0.244 g | 0.067 g | 4.86 g | 3.37 g |
| 1500 (33.3 g) | 0.806 g | 0.367 g | 0.100 g | 7.29 g | 5.05 g |
| 2000 (44.4 g) | 1.074 g | 0.489 g | 0.133 g | 9.72 g | 6.74 g |
| 20 g (100 mL) of Fish Oil 60% - MCT Oil 37% - Soya Oil 3% | | | | | |
| 100 (2.2 g) | 0.065 g | 0.027 g | 0.007 g | 0.48 g | 0.33 g |
| 500 (11.1 g) | 0.330 g | 0.133 g | 0.033 g | 2.43 g | 1.68 g |
| 1000 (22.2 g) | 0.659 g | 0.266 g | 0.067 g | 4.86 g | 3.37 g |
| 1500 (33.3 g) | 0.989 g | 0.400 g | 0.100 g | 7.29 g | 5.05 g |
| 2000 (44.4 g) | 1.319 g | 0.533 g | 0.133 g | 9.72 g | 6.74 g |
| 20 g (100 mL) of Fish Oil 60% - MCT Oil 36% - Soya Oil 4% | | | | | |
| 100 (2.2 g) | 0.077 g | 0.029 g | 0.007 g | 0.48 g | 0.33 g |
| 500 (11.1 g) | 0.391 g | 0.144 g | 0.033 g | 2.43 g | 1.68 g |
| 1000 (22.2 g) | 0.781 g | 0.289 g | 0.067 g | 4.86 g | 3.37 g |
| 1500 (33.3 g) | 1.173 g | 0.433 g | 0.100 g | 7.29 g | 5.05 g |
| 2000 (44.4 g) | 1.563 g | 0.578 g | 0.133 g | 9.72 g | 6.74 g |

TABLE 4-continued

EFA Intakes from Sample LipOmega-3 MCT Formulations
Fish Oil-MCT Oil-Soya Oil Mixtures

| Kcals/day (20% Fat) | *Linoleic | *Linolenic | AA | EPA | DHA |
|---|---|---|---|---|---|
| 20 g (100 mL) of Fish Oil 60% - MCT Oil 35% - Soya Oil 5% | | | | | |
| 100 (2.2 g) | 0.085 g | 0.031 g | 0.007 g | 0.48 g | 0.33 g |
| 500 (11.1 g) | 0.452 g | 0.156 g | 0.033 g | 2.43 g | 1.68 g |
| 1000 (22.2 g) | 0.904 g | 0.311 g | 0.067 g | 4.86 g | 3.37 g |
| 1500 (33.3 g) | 1.356 g | 0.467 g | 0.100 g | 7.29 g | 5.05 g |
| 2000 (44.4 g) | 1.807 g | 0.622 g | 0.133 g | 9.72 g | 6.74 g |

*Includes amounts from both Fish Oil and Soya Oil.

TABLE 5

Various Sample Concentrations of the Oil Phase While Maintaining a Phospholipid:Triglyceride ratio of 0.06

| Total Oil (g/100 mL) | Phospholipid (g/100 mL) | Fish Oil (%) | MCT Oil (%) | Soya Oil (%) |
|---|---|---|---|---|
| 5.0 | 0.30 | 90 | 10 | 0 |
| 7.5 | 0.45 | 80 | 20 | 0 |
| 10.0 | 0.60 | 80 | 15 | 5 |
| 12.5 | 0.75 | 70 | 30 | 0 |
| 15.0 | 0.90 | 70 | 29 | 1 |
| 17.5 | 1.05 | 60 | 40 | 0 |
| 20.0 | 1.20 | 60 | 36 | 4 |
| 22.5 | 1.35 | 50 | 50 | 0 |
| 25.0 | 1.50 | 50 | 47 | 3 |
| 27.5 | 1.65 | 40 | 60 | 0 |
| 30.0 | 1.80 | 31 | 69 | 0 |

While various embodiments are described herein, it will be appreciated that variations, modifications and other changes in form and detail may be made without departing from the spirit and scope of the disclosure. Such variations and modifications are to be considered within the purview and scope of the disclosure as defined by the appended claims.

REFERENCES

Mathru et al. Chest 1991; 99:426-29.
Prasertsom et al., Arch Dis Child 1996; 74:F95-98.
Ling et al. Digestive Disease Science 2001; 46:2484-9.
Driscoll et al. Lipid Emulsions in Parenteral Nutrition. In Clinical Nutrition: Parenteral Nutrition (Rombeau, Rolandelli, eds.) W. B. Saunders, 2001; pp. 35-59.
Driscoll et al. International Journal of Pharmaceutics, 2002; 240:1-10.
Bistrian, Journal of Parenteral and Enteral Nutrition, 2003; 27:168-75.
Gura et al. Clinical Nutrition 2005; 24:839-47.
Wales et al. Journal of Pediatric Surgery 2005; 40:755-62.
Paquot et al. Curr Opin Clin Nutr Metab Care 2005; 8:183-87,
Gura et al. Pediatrics 2006; 118:e197-e201.
Wanten et al. American Journal of Clinical Nutrition 2007; 85:1171-84.
European Pharmacopoeia 6.0, Monograph 1352, Omega-3 Acid Triglycerides,
Omega-3 acidorum triglycerida, 1893-95, 2008.
European Pharmacopoeia 6.0, Monograph 1912, Fish Oil, Rich in Omega-3 Acids, Piscis oleum omega-3 acidis abundans, 2554-56, 2008.
European Pharmacopoeia 6.0, Monograph 0868, Triglycerides, Medium-Chain, Triglycerida saturate media, 3122-24, 2008.
Driscoll et al, International Journal of Pharmaceutics, 2008a In press.
Wang et al. Journa of Parenteral and Enteral Nutrition, 2008; 32:236-41.
Simoens et al. American Journal of Clinical Nutrition 2008; 88:282-88.
Driscoll et al. Parenteral and Enteral Nutrition in the Intensive Care Unit. In Intensive Care Medicine (Irwin and Rippe, eds.), Wolters Kluwer, 2008b; pp. 2187-2201.

All of the references are herein incorporated by reference in their entirety to the same extent as if each individual reference were specifically and individually indicated to be incorporated herein by reference in its entirety.

The invention claimed is:

1. An oil-in-water emulsion having an oil phase and an aqueous phase, wherein the emulsion comprises an enriched fish oil and a medium chain triglyceride (MCT) oil, wherein the enriched fish oil is present at a concentration from about 31% to about 90% based on a total weight of the oil phase in the emulsion, wherein the MCT oil is present at a concentration from about 10% to 69% based on a total weight of the oil phase in the emulsion, and wherein the enriched fish oil comprises at least 45% by weight of EPA and DHA, and at least 60% by weight of n3-FA, based on the total weight of the enriched fish oil.

2. The emulsion of claim 1, wherein the amount of the MCT oil allows for the safe plasma clearance of the fish oil.

3. The emulsion of claim 1, wherein the emulsion further comprises soybean oil at a concentration up to about 10%, based on a total weight of the oil phase in the emulsion.

4. The emulsion of claim 1, wherein the MCT oil concentration allows for physicochemical stability of the emulsion as an extemporaneously prepared syringe for up to 12 hours at temperature up to 40° C.

5. The emulsion of claim 1, wherein the composition provides a source of calories that is equally nitrogen-sparing as a soybean parenteral oil-in-water emulsion.

6. The emulsion of claim 1, wherein the emulsion further comprises egg phospholipids.

7. The emulsion of claim 1, wherein the composition further comprises a sufficient amount of α-tocopherol as an anti-oxidant to protect the n-3 fatty acids.

8. A method of parenteral administration of the emulsion of claim 1, comprising parenterally administering the emulsion to a human body.

9. The emulsion of claim 1, wherein the oil phase of the emulsion consists of the enriched fish oil and the MCT oil.

10. The emulsion of claim 1, wherein the enriched fish oil is present at a concentration from 40% to 90% based on a total weight of the oil phase in the emulsion.

11. The emulsion of claim 1, wherein the enriched fish oil is present at a concentration from 50% to 90% based on a total weight of the oil phase in the emulsion.

12. The emulsion of claim 1, wherein the enriched fish oil is present at a concentration from 60% to 90% based on a total weight of the oil phase in the emulsion.

13. The emulsion of claim 1, wherein the enriched fish oil is present at a concentration from 70% to 90% based on a total weight of the oil phase in the emulsion.

14. The emulsion of claim 1, wherein the enriched fish oil is present at a concentration from 80% to 90% based on a total weight of the oil phase in the emulsion.

15. The emulsion of claim 1, wherein the MCT oil is present at a concentration from 10% to 40% based on a total weight of the oil phase in the emulsion.

16. The emulsion of claim 1, wherein the MCT oil is present at a concentration from 10% to 30% based on a total weight of the oil phase in the emulsion.

17. The emulsion of claim 1, wherein the MCT oil is present at a concentration from 10% to 20% based on a total weight of the oil phase in the emulsion.

18. The emulsion of claim 1, wherein the enriched fish oil is present at a concentration from 60% to 90% based on a total weight of the oil phase in the emulsion, wherein the MCT oil is present at a concentration from 10% to 40% based on a total weight of the oil phase in the emulsion.

19. The emulsion of claim 1, wherein the enriched fish oil is present at a concentration from 40% to 90% based on a total weight of the oil phase in the emulsion, wherein the MCT oil is present at a concentration from 10% to 40% based on a total weight of the oil phase in the emulsion.

20. The emulsion of claim 1, wherein the enriched fish oil is present at a concentration from 70% to 90% based on a total weight of the oil phase in the emulsion, wherein the MCT oil is present at a concentration from 10% to 30% based on a total weight of the oil phase in the emulsion.

* * * * *

UNITED STATES PATENT AND TRADEMARK OFFICE
CERTIFICATE OF CORRECTION

| | |
|---|---|
| PATENT NO. | : 8,241,672 B2 |
| APPLICATION NO. | : 12/382196 |
| DATED | : August 14, 2012 |
| INVENTOR(S) | : David F. Driscoll |

It is certified that error appears in the above-identified patent and that said Letters Patent is hereby corrected as shown below:

Column 4, Lines 65-67: delete "produce the "1-series" of prostaglandins, thromoboxanes and leukotrienes,"

Signed and Sealed this
Seventh Day of June, 2016

Michelle K. Lee
*Director of the United States Patent and Trademark Office*